United States Patent
Aoki et al.

(12)

(10) Patent No.: US 7,142,989 B2
(45) Date of Patent: Nov. 28, 2006

(54) COMPUTER SOFTWARE TO COMPUTER-DESIGN OPTIMUM OLIGO-NUCLEIC ACID SEQUENCE CANDIDATE FROM NUCLEIC ACID BASE SEQUENCES ANALYZED AND METHOD THEREOF

(75) Inventors: Yoshiaki Aoki, Mobara (JP); Mitsuyoshi Ishikawa, Mobara (JP)

(73) Assignee: Kabushikigaisha Dynacom, Mobara (JP)

( * ) Notice: Subject to any disclaimer, the term of this patent is extended or adjusted under 35 U.S.C. 154(b) by 306 days.

(21) Appl. No.: 10/176,293

(22) Filed: Jun. 20, 2002

(65) Prior Publication Data
US 2003/0023419 A1 Jan. 30, 2003

(30) Foreign Application Priority Data
Jun. 20, 2001 (JP) ............................. 2001-225181

(51) Int. Cl.
*G06N 3/12* (2006.01)
(52) U.S. Cl. ........................................................ 702/20
(58) Field of Classification Search ................ 702/19, 702/20; 435/6
See application file for complete search history.

(56) References Cited

FOREIGN PATENT DOCUMENTS
WO  WO 9411837  5/1994

OTHER PUBLICATIONS
Watson et al, Nature 171: 737 (1953).*

* cited by examiner

*Primary Examiner*—James Martinell
(74) *Attorney, Agent, or Firm*—Kathleen D. Rigaut; Roger W. Herrell; Dann Dorfman Herrell & Skillman (57) ABSTRACT

A computer software program to design an optimum oligo-nucleic acid base sequence candidate from nucleic acid base sequences being analyzed using a computer, the program comprising: a first command to receive the specification of respective tolerated ranges of double-chain bond temperature, base sequence length and GC content, and to store the information on the priority order of respective items in the memory; a second command, while extending the partial sequence in the aforementioned nucleic acid base sequences being analyzed, to determine whether or not a sequence in each length falls within respective tolerated ranges based on the priority items received by the aforementioned first command, and if it does fall within the ranges, to output the partial sequence in the applicable length as an oligo-nucleic acid base sequence candidate; and a third command to display, based on the aforementioned priority order, the oligo-nucleic acid sequence candidate outputted by the aforementioned second command along with the values of respective items.

18 Claims, 10 Drawing Sheets

List of sequences for Rn_Kidney

Hit 27 : Start 1 : End 10 : 1 / 3 Page  Next    You can set mark each clone.  OmniRen

| No. | Clone name | Length #probe/Tm/GC/length Start/length/Tm/oligo | | | | Definition |
|---|---|---|---|---|---|---|
| 1 | gnl|UG|Rn#S1075.L6 retried | 3320 | 72.88 77 | 72.88 50.70 | | Rat kidney Zn-peptidase aminopeptidase N mRNA, complete cds /cds=(19,2916) /gb=M25073 /ug=Rn.11132 /len=3320 |
|   |   | 1669/77/72.88 tgttatcactgtgaacaccagtacgggagaaattaccaggaacacttcctcctgacccacttccaaacctaccc | | | | |
| 2 | gnl|UG|Rn#S121731.L6 retried | 1989 | 72.85 50 77 | 72.92 50.00 | 56.90 58 80 /len=1989 | Rattus norvegicus kidney urea transporter (UT4) mRNA, complete cds /cds=(376,1758) /gb=AF031642 /gi=4104092 /ug=Rn.81195 |
|   |   | 1874/77/72.88 caaacccaccactattcctccctaatccgaggctgattcgttccctgcccagatctttataacaaccccttgtagc | | | | |
| 3 | gnl|UG|Rn#S155553.L6 retried | 1253 | --- | | | Rattus norvegicus Rat kidney prostaglandin EP3 receptor (Ptger3), mRNA /cds=(85,1173) /gb=NM_012704 /gi=6981433 /ug=Rn.10361 /len=1253 |
|   |   | --- | | | | |
| 4 | gnl|UG|Rn#S155608.L6 retried | 2547 | 72.88 50 77 | 72.89 50.70 | 56.90 58 /len=2547 | Rattus norvegicus Solute carrier family 4, member 1, anion exchange protein 1 (kidney band 3) (Slc4a1), mRNA /cds=(0,2546) /gb=NM_012651 /gi=6981549 /ug=Rn.32202 /len=2547 |
|   |   | 1844/77/72.88 tattccttgagtctcagatcacgcgctgattgtcagtgtcgaagatgatcaagggctccggcttccac | | | | |

List of sequences for Rn_Kidney

Hit 27 : Start 1 : End 10 : 1 / 3 Page Next You can set mark each clone. OmitReity

| No. | Clone name | Length/#probe/Tm/GC/length Start/length/Tm/oligo | | | Definition |
|---|---|---|---|---|---|
| 1 | gnl\|UG\|Rn#S1075.L6 retried | 3320 | 50 | 72.88 72.88 50.70 50.70 77 77 | Rat kidney Zn-peptidase aminopeptidase N mRNA, complete cds /cds=(19,2916) /gb=M25073 /gi=205108 /ug=Rn.11132 /len=3320 |
| | | 1669/77/72.88 tgttatcactgtgaacaccagtacgggagaaatctaccaggaacactctcctggacccccacttccaaacctaccc | | | |
| 2 | gnl\|UG\|Rn#S121731.L6 | 1989 | 50 | 72.85 72.92 50.00 56.90 77 80 | Rattus norvegicus kidney urea transporter (UT4) mRNA, complete cds /cds=(376,1758) /gb=AF031642 /g=4104092 /ug=Rn.81195 /len=1989 |
| | | 1874/77/72.88 caaaccaccactattcctccctaatccgaggctgattcgttccctcgcccagatctttataacaaccccttgtagc | | | |
| 3 | gnl\|UG\|Rn#S155553.L6 retried | 1253 | 50 | 72.81 72.92 50.00 59.60 77 80 | Rattus norvegicus Rat kidney prostaglandin EP3 receptor (Ptger3), mRNA /cds=(85,1173) /gb=NM_012704 /g=6981433 /ug=Rn.10361 /len=1253 |
| | | 851/77/72.88 gagacggctatccagcttatggggatcatgtgtactgtccgtctgtcggtcgccgctattgataatgatgctgaa | | | |
| 4 | gnl\|UG\|Rn#S155608.L6 retried | 2547 | 50 | 72.88 72.89 50.70 56.90 77 58 | Rattus norvegicus Solute carrier family 4, member 1, anion exchange protein 1 (kidney band 3) (Slc4a1), mRNA /cds=(0,2546) /gb=NM_012651 /g=6981549 /ug=Rn.32202 /len=2547 |
| | | 1844/77/72.88 tattccttgagtctcagatcaccacgctgattgtcagtaaacctgagcggaagatgatcaagggctccggcttccac | | | |

FIG. 12

COMPUTER SOFTWARE TO COMPUTER-DESIGN OPTIMUM OLIGO-NUCLEIC ACID SEQUENCE CANDIDATE FROM NUCLEIC ACID BASE SEQUENCES ANALYZED AND METHOD THEREOF

CROSS REFERENCE TO RELATED APPLICATIONS

This application claims priority under 35 U.S.C. 119 based upon Japanese Patent Application Serial No. 2001-225181, filed on Jun. 20, 2001. The entire disclosure of the aforesaid application is incorporated herein by reference.

BACKGROUND OF THE INVENTION

The present invention generally relates to a computer software program to design an optimum oligo-nucleic acid sequence candidate from nucleic acid base sequences being analyzed, and a method thereof.

To analyze the expression in cells of a gene that is the object of an experiment, an element called DNA chip is generally used. This DNA chip is comprised by arranging on a glass or silicon substrate, DNA fragments and/or RNA fragments having thousands to tens of thousands of different pieces of base sequence information.

This nucleic acid sequence of the plurality of DNA fragments and/or RNA fragments arranged on a DNA chip is called a capture, and is appropriately arranged so that binding, i.e., hybridization will occur with the specific gene, which is the object of the experiment. With this type of DNA chips, for instance, when a healthy cell has turned to a sick cell, it will be possible to find the expressed gene causing the illness by examining which gene in this cell has hybridization.

Here, the nucleic acid sequence of the aforementioned DNA fragments used as a capture is generally selected from a library. A library is an aggregate of DNA samples or an aggregate of cDNA samples prepared by cloning fragments of genes obtained from a cell or the like. Here, cDNA (complementary DNA) means the bases of the DNA sequences that can be combined with all bases of the messenger RNA; i.e., a DNA that is synthesized complementary to the messenger RNA.

However, it is difficult in terms of time, cost and technology for researchers to obtain actual samples that will be a capture, as they would have to obtain existing DNA fragments from cells. Therefore, researchers have recently begun using a method wherein an oligo-base sequence in a length of approximately several tens of bases is determined using the sequence information on the genome whose sequence information has already been read out, or the sequence information that identifies the sequence information of the poly A sequence terminal side (poly A is a sequence present in the RNA terminal of—AAAAOH) of the messenger RNA called EST (Expressed Sequence Tag), which is chemically synthesized and mounted on a substrate. Here, an oligo-nucleic acid means a nucleic acid having a relatively short base sequence (e.g., approximately 200 base pairs).

In the past, to determine an appropriate oligo-nucleic acid sequence, researchers partially extracted genes in a library or the gene as the object of an experiment, compared these sequences through visual observation, and searched for the similarities and differences present in the sequences. However, in these years, DNA chips and DNA arrays have higher levels of integration, meaning that more fragments of nucleic acids are integrated. Searches through visual observation are not realistic any more. Thus, computers are more commonly used to determine the base sequences of the nucleic acid fragments arranged on a substrate.

As a technology to realize this method, for instance, as disclosed in Patent No. WO 94/11837, an oligo-probe design station, which can design common probes and specific probes through computer processing using the data in gene sequence data sources, has been conventionally available.

However, this type of present computer-processing technology simply computes and provides hybridization strength modeling, upon which the user selects an appropriate probe. The technology will not be able to improve the accuracy of the bond temperature of the probe.

That is, when many different probes are designed for DNA chips or for other purposes, all of these probes must exhibit the same Tm. Tm value is the temperature at which 50 percent of the strands of the double helix are hydrogen bonded. This is determined by the GC content, and other parameters. However, the GC content varies according to the base sequence and its length. Therefore, to determine a sequence that has the specific sequence in the base length determined as the synthesis condition and also yields the appropriate temperature condition, it is very difficult to determine a sequence that meets all these prerequisites.

In the technology disclosed in the aforementioned Patent No. WO 94/11837, the strength of hybridization between oligo-nucleic acid sequence candidates and the specific gene is based on the Tm, and the information is presented to the user, so the user can easily select the probe to realize the optimum temperature condition. However, as the oligo-nucleic acid sequence candidates used in this technology were initially designed without considering the Tm condition, the aforementioned process does not mimimize the degree of differences of the Tm values of the oligo-nucleic acid sequence candidates. Thus, if we try to obtain a lot of probes from the oligo-nucleic acid sequence candidates, the degree of difference will be significantly large. According to the analyses made by the inventors, the error range of Tm of the oligo-nucleic acid base sequences obtained in the prior art will be as large as ±20 degrees. On the other hand, if we try to decrease this error range, there will arise a problem that we can only obtain insufficient number of oligo-nucleic acid base sequences. Meanwhile, another application that requires determination of oligo-nucleic acid sequence is designing of probes to provide a gene amplification means in the PCR (Polymerase Chain Reaction) method, among others. In the PCR method, to search for a specific base sequence part and to amplify that particular part, suitable probe base sequences as long as several tens of bases for the initial positions at both ends of the amplified sequence must be designed. Similarly to the case of designing the base sequence for a capture, in this application also, specific sequence primers must be designed so as not to have hydrogen bonding outside of the applicable part which is to be amplified. Further, the Tm must also be maintained under the same hybridization temperature condition.

For the aforementioned purpose, the designed probe must be a specific sequence that amplifies only the desired part of the applicable gene or the intermingled nucleic acids. Further, in some cases, a plurality of sequences may need to be concurrently amplified, and in such a case, it is necessary that each sequence is an appropriate sequence for the sequence to be amplified and such amplification is performed under similar Tm conditions.

A technology related to probe designs in this PCR method has been previously disclosed. However, because of the aforementioned reasons, this technology does not offer a solution that provides the appropriate Tm condition.

Further, computer processing allows efficient determination of the sequence parts that are specific only to the nucleic acid base sequence being analyzed through concurrent intercomparisons among a large number of nucleic acid base sequences. However, if the nucleic acid base sequences being compared include a sequence identical to the nucleic acid base sequence for an oligo-probe design, it will be impossible to determine the specific parts, thus to design the probe. In such a case, the aforementioned comparison must be repeated after determining and removing this duplicate base sequence, which means not only it takes time and trouble, but also the load on the computer was a cause for slowing down the whole processing speed.

As mentioned above, according to the prior art, there was a problem that, when a sequence is determined, which has the specific sequence in the base length determined as the synthesis condition as well as the appropriate temperature condition, it was very difficult to determine a sequence that meets all these prerequisites.

Further, according to the prior art, when a sequence identical to the nucleic acid base sequence being analyzed is registered in duplication as (i.e., has been duplicated in the database) a nucleic acid base sequence being compared, it is impossible to design an oligo-nucleic acid base sequence candidate. Thus, it was necessary to repeat the homology comparison after deleting the duplicate sequence registration.

This invention was made considering this situation. The object is to offer a system and a method, which can concurrently determine many oligo-nucleic acid sequences having a high level of accuracy in the values of Tm, GC content and base sequence length.

This invention was made considering this situation. The object is to offer a system and a method, which can concurrently determine many oligo-nucleic acid sequences having a high level of accuracy in the values of double-chain bond temperature, GC content and base sequence length.

A more detailed object of this invention is to offer a system and a method, wherein, when oligo-nucleic acid sequences are determined, the desired tolerated design range and the priority items are specified, and the oligo-nucleic acid sequences that meet the condition can be determined and displayed.

Another detailed object of this invention is to offer a system and a method, wherein oligo-nucleic acid base sequences can be determined without repeating homology comparison from the beginning, even when a sequence identical to the nucleic acid base sequence being analyzed is registered in duplication as the nucleic acid base sequence being compared.

BRIEF SUMMARY OF THE INVENTION

To address the aforementioned issue, according to the first aspect of this invention, a computer software program to design, using a computer, at least one oligo-nucleic acid sequence candidate which binds a nucleic acid base sequences being analyzed is offered; wherein the program comprises a first command that inputs tolerated ranges of Tm, base sequence length and GC content, and stores this information in the memory and sets a priority order of each item; a second command that, while extending the length of a partial sequence in the aforementioned nucleic acid base sequences being analyzed, determines whether or not the extended partial sequence in each length falls within specified tolerated ranges in the aforementioned first command, and if it does fall within the ranges, outputs the applicable length of partial sequence as an oligo-nucleic acid base sequence candidate; and a third command that, based on the aforementioned priority order, displays the oligonucleic acid sequence candidate outputted by the aforementioned second command along with the values of Tm, base sequence length and GC content.

According to this configuration, based on the inputted tolerated ranges of Tm, base sequence length and GC content, an oligo-nucleic acid sequence that meets these conditions can be obtained while varying the starting point and the length of the sequence candidate. In this manner, it will be possible to determine/output many oligo-nucleic acid sequence candidates that meet the aforementioned tolerated range condition.

Here, according to a preferred embodiment of this invention, in the aforementioned program, the aforementioned second command extends the aforementioned partial sequence so that the applicable nucleic acid base sequence being analyzed will include specific sequence parts based on the homology comparison between the nucleic acid base sequence being analyzed and the other plurality of nucleic acid base sequences; and all of the aforementioned homology comparison results are stored in the memory. This program preferably further comprises a fourth command that, from among the aforementioned homology comparison results, voids any comparison results in the aforementioned memory so as to renew the comparison results in the aforementioned memory.

Also, this program preferably further comprises a fifth command that, when outputting of oligo-nucleic acid sequence candidates for any or all nucleic acid base sequences being analyzed has been completed, notifies specified users of the completion of the outputting.

According to the second aspect of this invention, a computer software program to execute, using a computer, homology comparison of a plurality of registered nucleic acid base sequences, and to design, based on the comparison results, an oligo-nucleic acid sequence candidate optimum for a specific nucleic acid base sequence being analyzed is offered; wherein the computer software program comprises a first command to store the comparison results among all nucleic acid base sequences in the memory and the second command to void any comparison results from among the aforementioned comparison results so as to renew the aforementioned comparison results.

According to this configuration, for instance, even in a case where the sequences for comparison include, as a sequence for reference, a nucleic acid base sequence that is an identical sequence to the nucleic acid base sequence being analyzed, the comparison results can be easily voided. Therefore, designing of oligo-nucleic acid base sequences can continue without repeating homology comparison from the beginning.

Here, according to an embodiment, this program further comprises a third command that designs an oligo-nucleic acid sequence optimum for a specific nucleic acid base sequence being analyzed based on the aforementioned renewed comparison results.

Further, according to another embodiment, in the aforementioned program, the second command comprises both a command to retrieve the aforementioned comparison results from the aforementioned memory and display on the screen the homologous regions of each sequence compared arranged in a predetermined format with the aforementioned base sequence being analyzed, and a command to select base sequences to be voided on the screen thereby to void the comparison results with such homologous base sequences.

Also, according to another embodiment, the aforementioned program further comprises a fourth command to detect, based on the comparison results in the aforementioned memory, that the aforementioned plurality of nucleic acid base sequences have duplicate registration (i.e., have been deposited in the database in duplicate) of a nucleic acid base sequence and is identical to the nucleic acid base sequence being analyzed. The aforementioned second command renews the aforementioned comparison results by voiding in the memory the comparison results between duplicate nucleic acid base sequences detected based on the aforementioned fourth command.

Also, the aforementioned program further comprises a fifth command to input the tolerated ranges of Tm, base sequence length and GC content and store this information in the memory and designate a priority order of each item; a sixth command to design, based on the aforementioned comparison results and the tolerated ranges and the priority item received by the aforementioned fifth command, oligo-nucleic acid sequence candidates optimum for the nucleic acid base sequence being analyzed; and a seventh command to display in the aforementioned priority order the plurality of oligo-nucleic acid sequence candidates designed by the aforementioned sixth command.

According to the third aspect of this invention, a method to design, using a computer, optimum oligo-nucleic acid base sequence candidates from the nucleic acid base sequences being analyzed is offered; wherein the method comprises a first step to input specified tolerated ranges of Tm, base sequence length and GC content and to store this information in the memory and assign a priority order of the respective parameters; a second step to determine, while extending partial sequences in the aforementioned nucleic acid base sequences being analyzed, whether or not the partial sequence in each length falls within the specified tolerated ranges based on the settings inputted by the aforementioned first command, and if it does fall within the ranges, to output the applicable length of partial sequence as an oligo-nucleic acid sequence candidate; and a third step to display, based on the aforementioned priority order, the oligo-nucleic acid sequence candidates outputted by the aforementioned second command along with the values of respective items.

According to this configuration, a processing method that is executed by the program pertaining to the aforementioned first aspect will be offered.

According to the fourth aspect of this invention, a processing method to execute, using a computer, homology comparison of a plurality of registered nucleic acid base sequences (i.e., previously deposited sequences), and to design oligo-nucleic acid sequence candidates having optimum binding for a specific nucleic acid base sequence being analyzed based on the comparison results is offered; wherein the method comprises both a first step to store in the memory the comparison results among all nucleic acid base sequences and a second step to void in the aforementioned memory any comparison results from among the aforementioned comparison results, thereby to renew the aforementioned comparison results.

According to this configuration, a processing method that is executed by the program pertaining to the aforementioned second aspect will be offered.

Having described the invention, the following examples are given to illustrate specific applications of the invention including the best mode now known to perform the invention. These specific examples are not intended to limit the scope of the invention described in this application.

DETAILED DESCRIPTION OF THE PREFERRED EMBODIMENTS

A preferred embodiment of the present invention will be described in detail below with reference to the accompanying diagrams. The diagrams illustrate only an example of the embodiments of the invention. Unless otherwise specified, the terms in the explanation will bear the meaning that is ordinarily used by those skilled in the art wherein this invention belongs.

Figure 1:
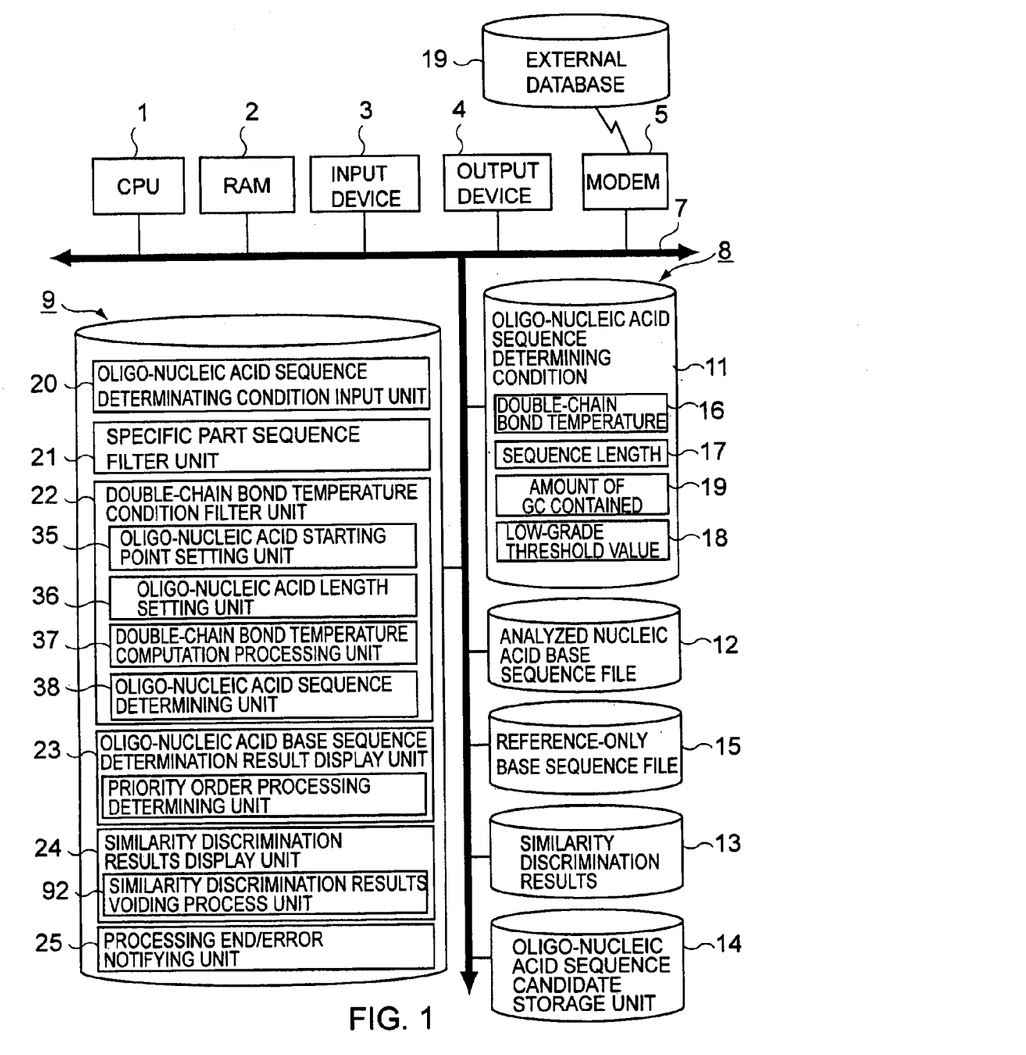
FIG. 1 is a system configuration diagram illustrating an embodiment of this invention.

FIG. 1 is a block diagram of the whole system of the present invention.

This system comprises a data storage unit 8 and a program storage unit 9 both connected to a bus 7, which comprises a CPU 1, a RAM 2, input devices 3 including a keyboard and a mouse, output devices 4 including a display and a printer, and a modem 5 being connected.

In the data storage unit 8, if we list only the components pertinent to this invention, the oligo-nucleic acid sequence determining condition 11, the analyzed nucleic acid base sequence file 12, the reference-only base sequence file 15, the similarity discrimination results 13 of the nucleic acid base sequences analyzed and the oligo-nucleic acid sequence candidates 14 will be stored.

In the oligo-nucleic acid sequence determining condition 11, at least the Tm 16, the oligo-nucleic acid length condition 17, the low-grade threshold value 18 and the GC content 19 will be stored. In this embodiment, the Tm 16 will be set as a range, based on a desired Tm, of, for instance, the highest tolerated temperature $Tmu=Tm+3°$ C., and the lowest tolerated temperature $Tml=Tm-3°$ C. The length condition 17 and the GC content will be set respectively as ranges of, for instance, 50~100 base length (shortest is 50 base length, and longest is 100 base length) and 40~60% GC content to effectively prevent mis-hybridization.

The low-grade threshold value 18 is the expressed ratio of the number of sequences in the non-specific part allowed to be contained in an oligo-nucleic acid sequence candidate to the number of sequences in the specific part contained in the same oligo-nucleic acid sequence candidate. In this embodiment, it is, for instance, set to 50%. Then, the oligo-nucleic acid sequences partially containing sequences in the non-specific part is outputted as "low grade," and will be distinguished from oligo-nucleic acid sequence candidates fully composed of the specific part.

The analyzed nucleic acid base sequence file 12 consists of data containing a plurality of nucleic acid base sequences, which the user has been interested in and has collected. The aforementioned reference-only base sequence file 15 consists of base sequences exclusively for reference, which have been optionally added/set from external databases such as the cDNA/EST database. These sequence files 12, 15 may also contain data downloaded from one or more specific external databases 19 connected through the aforementioned modem 5.

The aforementioned similarity discrimination results 13 are the results including the specific sequence parts and non-specific sequence parts of each base sequence analyzed, which are identified by distinguishing between the similarities within the aforementioned nucleic acid base sequences analyzed and the similarities between the nucleic acid sequences analyzed and the reference-only base sequences. Then, the aforementioned oligo-nucleic acid sequence candidates 14 are oligo-nucleic acid sequence candidates in various base lengths computed based on the aforementioned similarity discrimination results 13 and the aforementioned oligo-nucleic acid sequence determining condition 11.

Meanwhile, in the program storage unit 9, if we list only the components pertinent to this invention again, roughly divided, an oligo-nucleic acid base sequence determining condition input unit 20, a specific partial sequence filter unit 21, a Tm condition filter unit 22, an oligo-nucleic acid base sequence determination result display unit 23, a similarity discrimination results display unit 24 and a processing end/error notifying unit 25 are stored.

In actuality, these components 20~25 are composed of a certain region secured in a recording medium such as a hard disk, or one or more program commands of computer software stored in the region, and any time when the aforementioned CPU 1 calls them onto the RAM 2 to run them, they will perform the function of this invention. Next, detailed configuration and function of the aforementioned components will be explained along with the actual oligo-nucleic acid base sequence determining procedure that is executed by this system.

Figure 2:
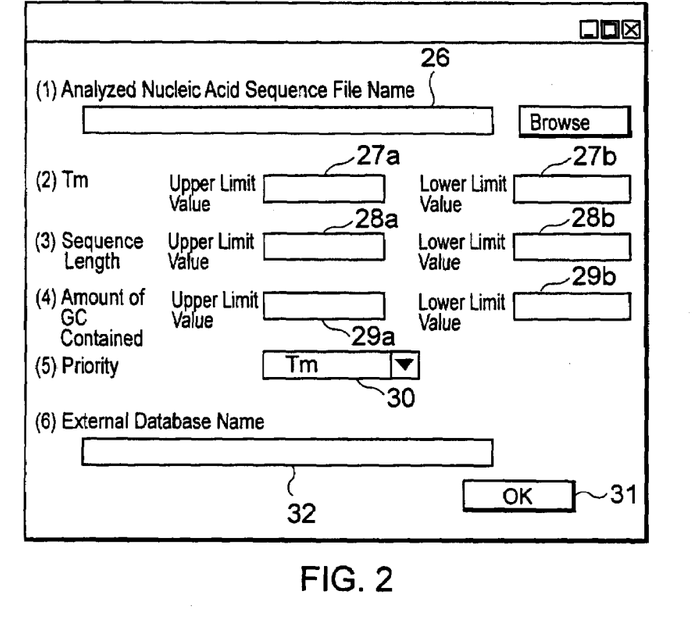
FIG. 2 is a type diagram illustrating a nucleic acid base sequence being analyzed.

The aforementioned oligo-nucleic acid base sequence determining condition input unit 20 displays a screen for the user to input the condition on, for instance, the aforementioned display (output device 4). An example of this screen is indicated in FIG. 2. The screen includes an input box 26 for analyzed nucleic acid base sequence file name, input boxes 27a, 27b respectively for the upper limit and the lower limit double-chain bond temperature values, input boxes 28a, 28b respectively for the shortest and the longest values for the sequence length condition, input boxes 29a, 29b respectively for the minimum and the maximum values for the GC content, a pull-down box 30 for entering priority items and an input box 32 to specify the external database name. When the user enters or selects a value in respective input boxes 16~32 and presses the OK button 31 afterward, the analyzed nucleic acid base sequence files 12, 15 (external database 19) will be specified, and at the same time, the aforementioned oligo-nucleic acid sequence determining condition 11 will be stored in the aforementioned data storage unit 8.

The aforementioned specific partial sequence filter unit 21 has the function of reading information on each nucleic acid base sequence from the analyzed nucleic acid base sequence file 12 and from the reference-only base sequence file 15, and evaluating the similarities between each of the base sequences. The similarities are evaluated by simply comparing the character strings corresponding to the base. Here, as accurate one-to-one comparisons of similarities and differences are required of the base sequences to select appropriate sequences, a homology search including insertion and deletion, which is frequently used in gene sequence search, is not suitable. Sequences are preferably compared strictly without assuming insertion or deletion. Therefore, a search means that does not correspond to gaps is suitable.

If the BLAST method is used, the method before correspondence to gaps should be used, and the expected value (E-value) that varies depending on the database size should be set considerably loose (high) so that even a small partial concordance can be retrieved. Here, E-value means the expected value at which a fragment of the gene, which is the object of the experiment, can be found when a specific size of database is searched. Furthermore, referring to the scores of the fragments found, those with a higher score than the score provided by the threshold value are set as similar sequences. Here the score means the quantity that corresponds to the level of concordance (the length of sequence in concordance or the level of similarity) of the object of comparison.

Figure 3:
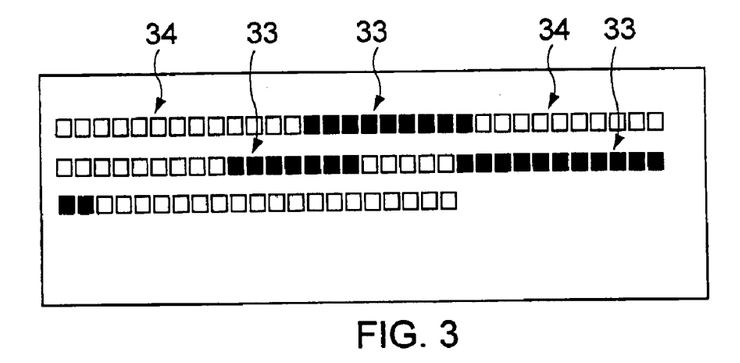
FIG. 3 is a type diagram illustrating the procedure for determining an oligo-nucleic acid sequence candidate from base sequences being analyzed.

FIG. 3 illustrates one of the nucleic acid base sequences analyzed. In this figure, for the convenience of explanation, one nucleic acid base sequence analyzed is folded and displayed in several lines. All base information A, C, G, T(U) of the nucleic acid is indicated with a square.

The aforementioned specific sequence filter unit 21 will register, according to the homology search by the aforementioned BLAST method, sequences that were partially homologous to other nucleic acid base sequences analyzed or the reference-only base sequences, as non-specific partial sequences (or common partial sequences). In this FIG. 3, the parts that are colored black (indicated with Key 33 in the figure) indicate non-specific partial sequences. Therefore, the white squares (indicated with Key 34 in the figure) indicate specific partial sequences.

Incidentally, without using the BLAST method, a technique of character string concordance search may also be applied, wherein an appropriate sequence width is set, which is used as the window width, and shifted for comparisons.

Using a method such as described above, parts that are in concordance with each other at or above a desired threshold value are retrieved, and the hit results are registered as non-specific partial sequences (33). At this time, the score based on the length of the character string in concordance and the information on the position of concordance will also be registered. If necessary, repeated sequence parts are preferably excluded as nonspecific partial sequences.

Then, this specific partial sequence filter unit 21, after comparing all nucleic acid sequences analyzed, tabulates the results (parts with high levels of concordance/similarity) obtained through the comparison for each nucleic acid base sequence analyzed. In this manner, the remaining sequence parts after deleting nonspecific sequence parts 33 with a high level of similarity will be outputted as the filtered specific partial sequences (or different partial sequences) (parts indicated with Key 34 in the figure). FIG. 3 illustrates the result of such filtering. The base sequences after this similarity discrimination will be stored in the data storage unit 8 as the aforementioned similarity discrimination results 13.

The Tm condition filter unit 22 performs the function of determining oligo-nucleic acid sequences in the length that falls within the specified Tm condition from among the nucleic acid base sequences obtained as the aforementioned similarity discrimination results (13)

This Tm condition filter unit 22, as illustrated in FIG. 1, comprises a starting point setting unit 35, a length setting unit 36, a Tm computing unit 37, and an oligo-nucleic acid sequence candidate determining unit 38.

The Tm computing unit 37 computes the Tm of the oligo-base sequence, which starts from the starting point set by the aforementioned starting point setting unit 35 and has the length set by the aforementioned length setting unit 36. As a method to compute Tm, for instance, the Nearest-Neighbor method (Santa Lucia, J. Jr. Proc. Nati. Acad. Sci. USA, 95, 1460–1465, 1998) is used for those with 36 bases or less; and for those with 37 bases or more, the method described in J. Sambrook, E. F. Fritsch, T, Molecular Cloning, p. 11.46: a laboratory Manual, Cold Spring Harbor Laboratory Press, 1989 is preferably used at the present point. However, naturally, any other methods may be used.

The aforementioned oligonucleic acid sequence candidate determining unit 38 receives this computation result each time the aforementioned Tm computing unit 37 computes the Tm. Then, it outputs oligo-nucleic acid sequences that fall within the specified ranges of Tm, GC content and length inputted as the aforementioned oligo-nucleic acid sequence determining condition 11 as the candidates. By applying this process while shifting the starting point and extending the length of the sequence as described above, various lengths of oligo-nucleic acid base sequence candidates that fall within the desired Tm condition will be obtained.

Next, using FIG. 4~FIG. 6, one of the nucleic acid base sequences analyzed and the procedure to retrieve oligo-nucleic acid base sequence candidates from it while estimating the temperature will be described in detail.

Figure 4:
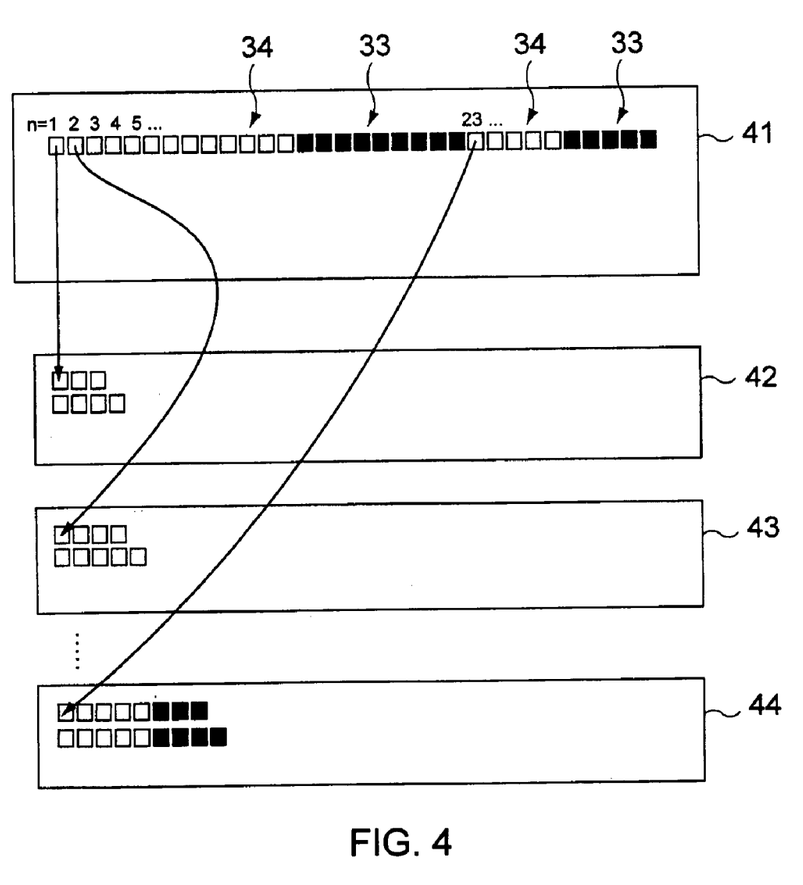
FIG. 4 illustrates an input screen to input the conditions for determining an oligo-nucleic acid sequence.
Figure 5:
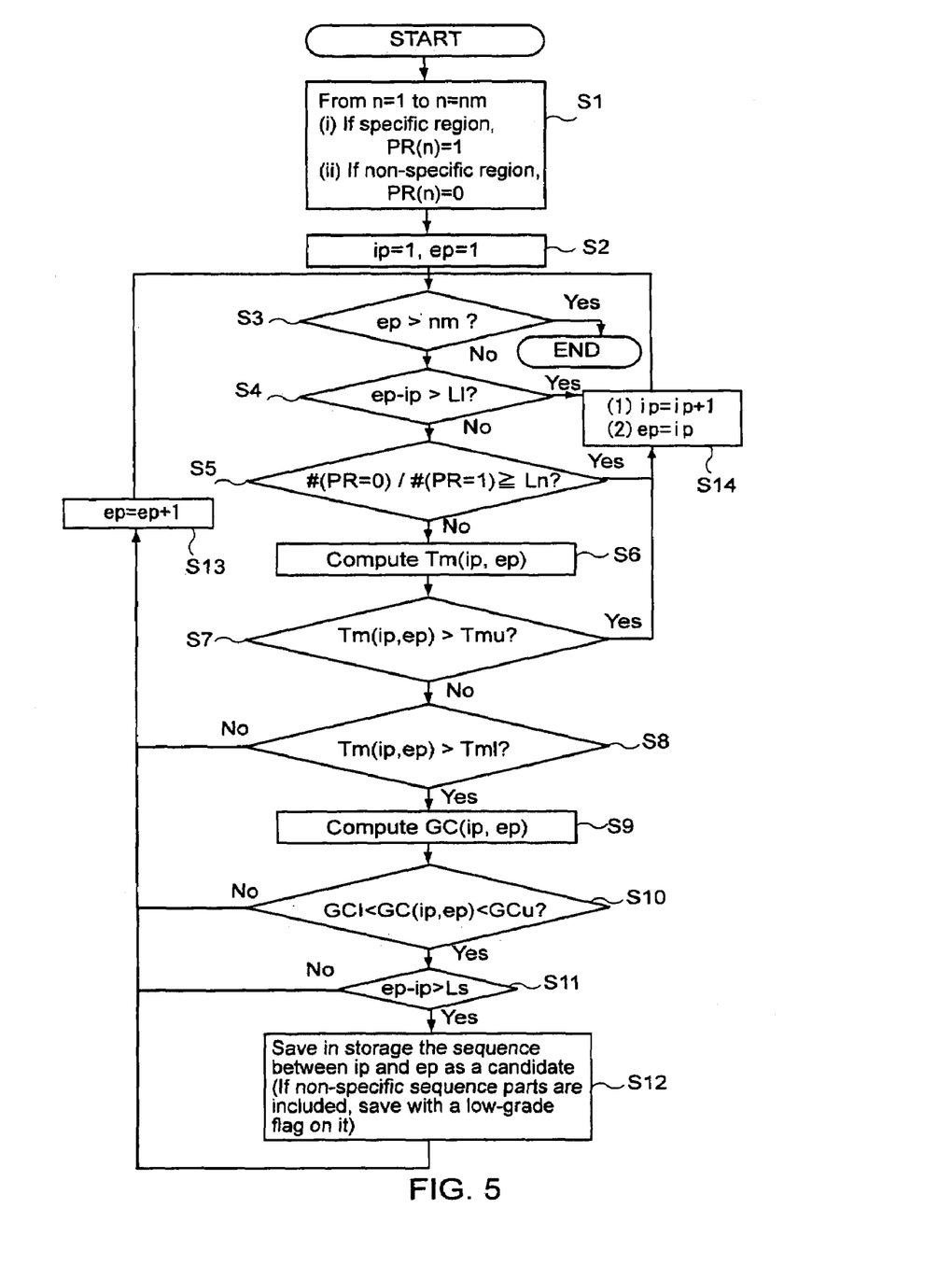
FIG. 5 is a flow chart to explain the procedure for determining an oligo-nucleic acid sequence.

FIG. 4 is a type diagram illustrating this procedure.

In the figure, Key 41 indicates a similarity discrimination result like FIG. 3. In the sequences in this similarity discrimination result, the GC content and the Tm are computed successively from the starting part (n=1) in the first specific sequence part 34 while extending the length of the sequence. Then, when the sequence part has entered the pre-specified ranges of length, GC content and Tm, the sequence part is saved as an oligonucleic acid base sequence candidate as illustrated in 42. Then, while extending the sequence part to a point that surpasses the upper limit temperature Tmu, the candidates are being saved.

In this example, to simplify the illustration, those that are shorter than the length 17 set under the aforementioned condition are displayed as the candidates. In actuality, on the other hand, base sequences that meet the aforementioned set length condition will be left as the candidates. Then, when the upper limit Tmu has been reached, the initial position is shifted by one, and from the new starting part, the Tm will be computed in the same manner while successively extending the length of the sequence. In this manner, another group of candidates will be obtained as indicated with Key 43 in the figure.

Incidentally, when the part 34 of specific partial sequence is so short that the number of obtained candidates in the length that meets the aforementioned Tm condition is too small within this specific partial sequence, base in the non-specific sequence part with a small score will be gradually added to extend the length to one that meets the Tm condition; which is then displayed as an obtained low-grade candidate for oligonucleic acid base sequence. See Key 44. Specifically, referring to the afore-mentioned low-grade threshold value 18, the sequence is extended until the aforementioned non-specific region part surpasses this threshold value 18, and when it has surpassed the value, the initial position will be shifted.

The lengths of oligo-nucleic acid base sequences outputted as candidates are preferably lengths between 50 bases and 100 bases. In this embodiment, by providing a specific length such as a value between 60 and 70 or so as the threshold value, it will be probabilistically difficult for samples other than the applicable nucleic acid base sequences analyzed to cause hybridization to the probe, thus noise can be reduced.

Next, referring to the flow chart in FIG. 5, actual processing procedure in this system will be explained.

In the explanation and the flow chart below, each of the constants and variables are defined as follows:

n: Sequence number from the starting of each base nucleic acid base sequence (1, 2, 3, 4 . . . in FIG. 4) nm: Last base number of each base nucleic acid base sequence PR(n): In case of specific sequence part=1; In case of non-specific sequence part=0 ip: Initial position of oligo-nucleic sequence for which Tm is obtained ep: Ending position of oligo-nucleic acid sequence for which Tm is obtained Tm(ip, ep): Tm of the sequence between the initial position ip and the ending position ep Tmu: Upper limit value for tolerated Tm Tml: Lower limit value for tolerated Tm Ls: Shortest sequence length Ll: Longest sequence length Ln: Low-grade threshold value (Ratio of tolerated non-specific region length to specific sequence part) GC(ip, ep): GC content between the initial position ip and the ending position ep Gcu: Upper limit value of Tolerated GC content GCl: Lower limit value of Tolerated GC content First in Step S1, the PR value will successively be set while scanning from n=1 to n=nm. In this manner, each base in the sequence analyzed will be set as follows: If it is present in the specific partial sequence region, PR (n)=1 (white part 34 in FIG. 2); and if it is present in the non-specific partial sequence, PR (n)=0 (Black part 33 in FIG. 2).

Next, in Step S2, as the initial values for the initial position number ip and the ending position number ep, ip=1 and ep=1 will be set. In the next step S3, it is determined whether or not the ending position number has reached the last base number nm of the applicable nucleic acid base sequence; and if it has not reached the number, in the following step S4, it is determined whether or not the length of the partial sequence between ip and ep has surpassed the upper limit value Ll of the aforementioned sequence length.

If it has surpassed the value, the process will proceed to the step S12 (will be explained later), wherein the initial position will be shifted. If it has not surpassed the value, in Step S5, based on the aforementioned low-grade threshold value Ln, it will be checked whether the ratio of specific sequence part and non-specific partial sequence in the sequence between ip and ep is larger than Ln. In this example, Ln is 50%. Therefore, it is checked whether or not the ratio of the number of bases having PR (n)=1 to the number of bases having PR (n)=0 is larger than 50% in the sequence between ip and ep.

If it is larger, it will proceed to the step S14 wherein the initial position will be shifted. If it is smaller, the process will proceed to the step SG to obtain a Tm. In Step S6, the Tm (ip, ep) value for the sequence between ip and ep is computed, and the process will proceed to Step S7. In Step S7, it is determined whether or not the Tm (ip, ep) value is larger than the upper limit value Tmu. If it is larger, without leaving this sequence as a candidate, the process will proceed to the step S12 to shift the aforementioned initial position. If it is smaller, the process will proceed to the next step S8. In general, the longer the sequence, the higher the Tm value; thus when the Tm (ip, ep) value is higher than Tmu, extending the partial base sequence further is meaningless.

Next, in Step 58, it is checked whether the value of Tm (ip, ep) is higher than Tml or not. If it is higher, the Tm of this sequence is determined to fall between the upper limit value Tmu and the lower limit value Tml, and the process will proceed to the next step S9.

In Step S9, the GC content of the sequence between ip and ep; i.e., GC (ip, ep)is computed. Then, in Step S10, whether or not GC (ip, ep) is higher than the lower limit value GCl of the tolerated GC content and lower than the upper limit value Gcu is checked. If it is within the range, the process proceeds to Step S11.

In this step S11, it is determined whether or not the length of this sequence is longer than the lower limit Ls; if it is longer, this sequence (ip, ep) will be determined to be an oligo-nucleic acid sequence candidate, and will be stored in the aforementioned data storage unit 8. Further, if non-specific sequence part is contained in a part of this oligo-nucleic acid sequence candidate (when the ratio in Step S5 is 1 or higher), said sequence will be saved with a low-grade flag on it (Step S12).

When the Tm is determined lower than the lower limit value in Step S8, or when the sequence length is determined too short in Step S11, the process will proceed to Step S13, and the aforementioned ending position number will increase by one (ep=ep+1). Then, the aforementioned steps S3~S12 will be repeated. Here, to compute the aforementioned Tm (ip, ep), generally, use of the previous computation result Tm (ip, ep=1) will allow stacking, thus faster computation.

By repeating these steps, various lengths of base sequences based on the aforementioned starting point will be saved as candidates.

Meanwhile, if the sequence is determined not to meet the condition in the aforementioned steps S4, S5 or S7, the process of shifting the initial position will be applied in Step S14. Thus, in S14, (1) the starting point is shifted by one, thus here, the starting point number ip increases by one (ip=ip+1); (2) the ending position number ep is adjusted to this initial position number ip (ep=ip). In this manner, the starting point will be shifted, and the length will be reset. Then, by repeating the aforementioned steps S3~S12, oligo-nucleic acid sequences with a shifted initial position will be successively outputted as candidates.

Incidentally, if the starting point has entered the non-specific region 33, as Ln will be determined to be 100% in the aforementioned step S5, the aforementioned Tm will not be computed until it comes out of this non-specific region. In this manner, the non-specific region will be skipped. That is, while skipping the non-specific partial sequence regions, only the partial base sequences whose Tm falls between Tml and Tmu can be saved in the storage.

Then, when the initial position ip has shifted to the ending position nm of this nucleic acid base sequence being analyzed, this fact will be detected in the aforementioned step S3, and all the steps will end.

According to this type of processing, based on the Tm, candidates can be determined while varying the lengths of oligo-nucleic acid base sequences; thus even when designing is made so that the Tm will fall within a narrower range, many oligo-nucleic acid sequences can be obtained.

The oligo-nucleic acid base sequence candidates obtained in this manner will be retrieved from the aforementioned data storage unit 8 by the oligo-nucleic acid base sequence determination result display unit 23 and will be displayed on a display (output device 4).

Figure 8:
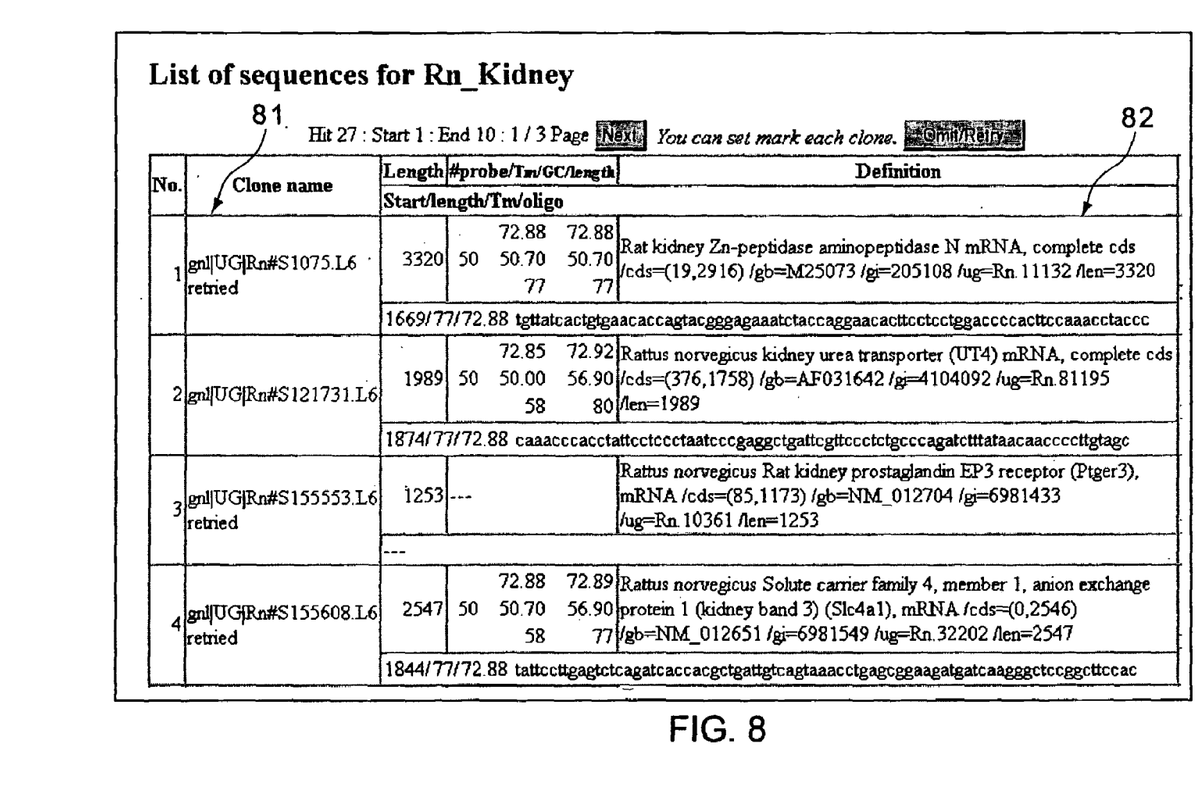
FIG. 8 illustrates a screen display of the design results of oligo-nucleic acid base sequences.

These designing results will basically be displayed for each nucleic acid base sequence analyzed. Further, the priority order process determination unit illustrated in FIG. 1 will display the most appropriate oligo-nucleic acid base sequence candidate based on the priority items selected in FIG. 2. FIG. 8 illustrates an example of the display of this designing result. This display example is in a table format, wherein a nucleic acid base sequence being analyzed 81 and the optimum oligo-nucleic acid base sequence 82 that corresponds to the sequence are displayed in each row.

Figure 9:
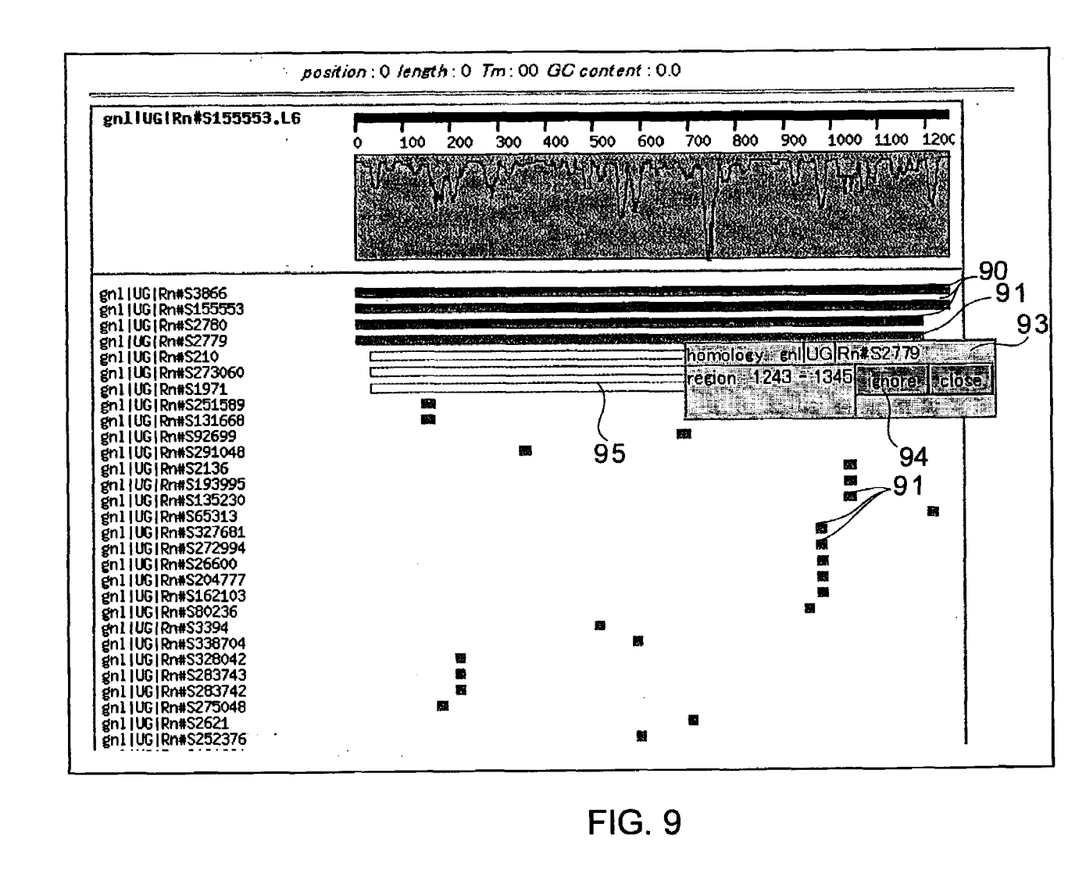
FIG. 9 illustrates a screen display of multiple alignments of similarity discrimination results.

Incidentally, as no oligo-nucleic acid base sequence is indicated for the base sequence S155553.L6 in the third row of the designing results illustrated in this figure, we can see that it was impossible to make an appropriate design for this sequence using the specified parameters of Tm, base sequence length and GC content. In this embodiment, if the user clicks with a mouse the part of S155553.L6, the aforementioned similarity discrimination results display unit 24 will start, and the similarity discrimination results 13 for this base sequence being analyzed will be retrieved from the aforementioned data storage unit 3, and a multiple alignment display will be made as illustrated in FIG. 9.

Figure 10:
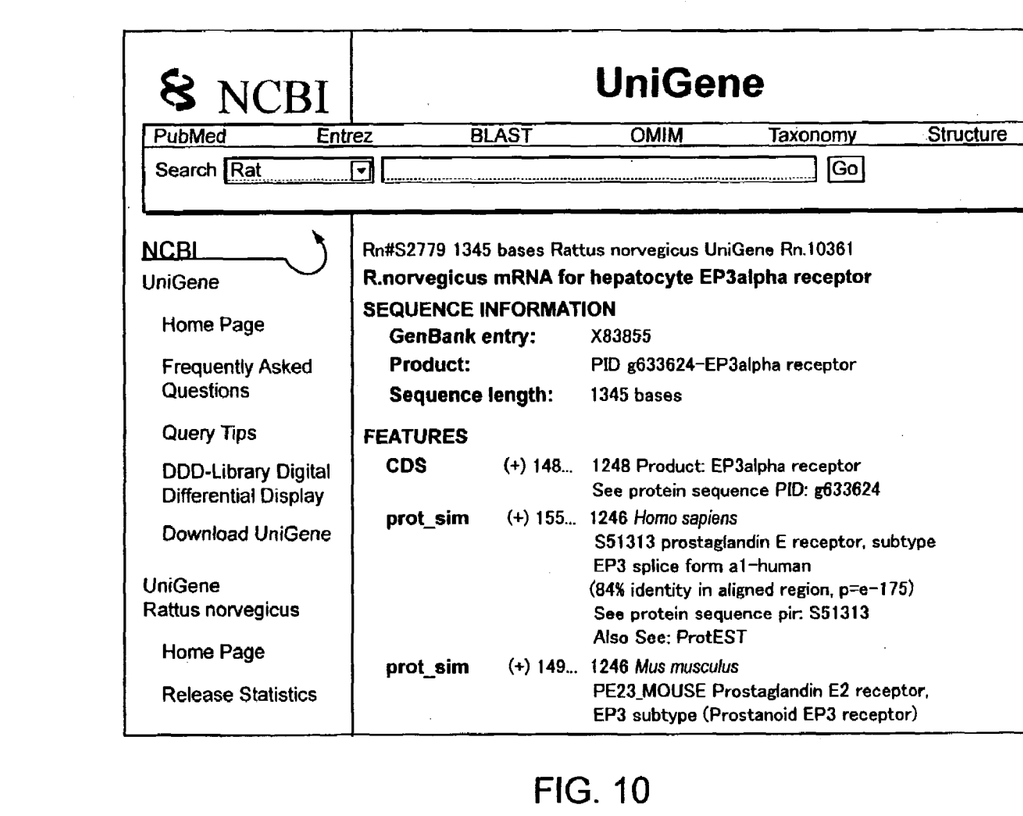
FIG. 10 illustrates a screen display of information on nucleic acid base sequences.

In this embodiment, the sequence part that is determined to be identical to the the base sequence being analyzed will be indicated in a light-blue band as indicated with Key 90 in the figure. In the system of this embodiment, base sequences that duplicate the base nucleic acid sequence being analyzed 90 percent or more will be determined as duplicate sequences, and be indicated in light blue as mentioned above. Further, if we move the mouse pointer onto the duplicate nucleic acid base sequence and double-click the mouse, the screen display illustrated in FIG. 10 will open. From the information in this screen also, we can confirm that this nucleic acid base sequence was registered in duplication (i.e., is identical to a previously deposited sequence).

When duplicate nucleic acid base sequences are registered in this manner, as no specific parts can be determined for the base nucleic acid sequence being analyzed, it will be impossible to design an appropriate oligo-nucleic acid base sequence. Therefore, in the system of this embodiment, the similarity discrimination results with the base sequences determined as duplication in this manner will be automatically voided to design an oligo-nucleic acid base sequence. Therefore, a case wherein no oligo-nucleic acid base sequence can be appropriately designed in this embodiment indicates a situation wherein sequences that have not been determined to duplicate by this system actually contain base sequences that duplicate in a considerable portion (90% or lower).

In the aforementioned multiple alignment display, the sequence parts with 90% or less duplication percentage are indicated in gray. See Key 91. Looking at this multi-alignment display, the operator visually picks up those with a considerably higher duplication percentage from the gray band, and manually voids them. Specifically, if he moves the mouse pointer onto the duplicate nucleic acid base sequence and right-click the mouse, the similarity discrimination results voiding process unit 92 provided in the aforementioned similarity discrimination results display unit 24 will open a pop-up window such as indicated with Key 93 in FIG. 9; and by selecting the Ignore button 94 here, the similarity discrimination results related to this base sequence can be voided. The voided results will be indicated with frames with white inside as indicated with Key 95 in the figure. Incidentally, even if a discrimination result is voided once in this manner, if the similarity discrimination result indicated with this frame with white inside is clicked, a pop-up window ill to resume its effectiveness will open, and it will be possible to return it to the original state.

Figure 11:
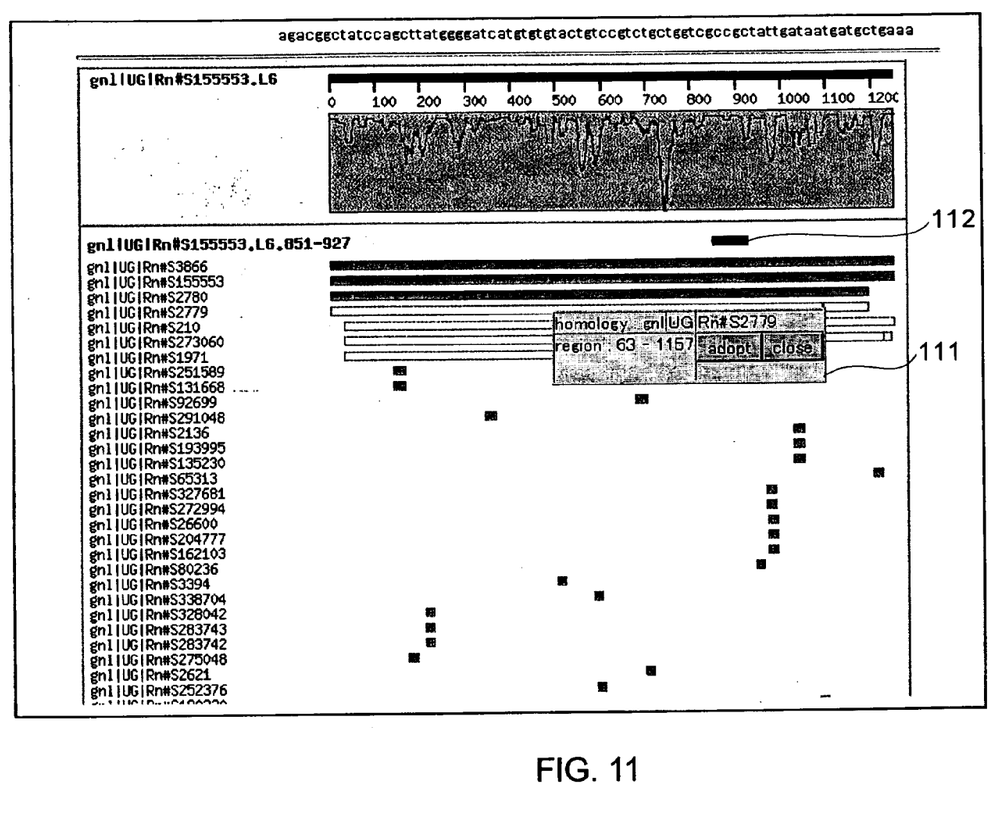
FIG. 11 illustrates a screen display of multiple alignments of similarity discrimination results.
Figure 12:
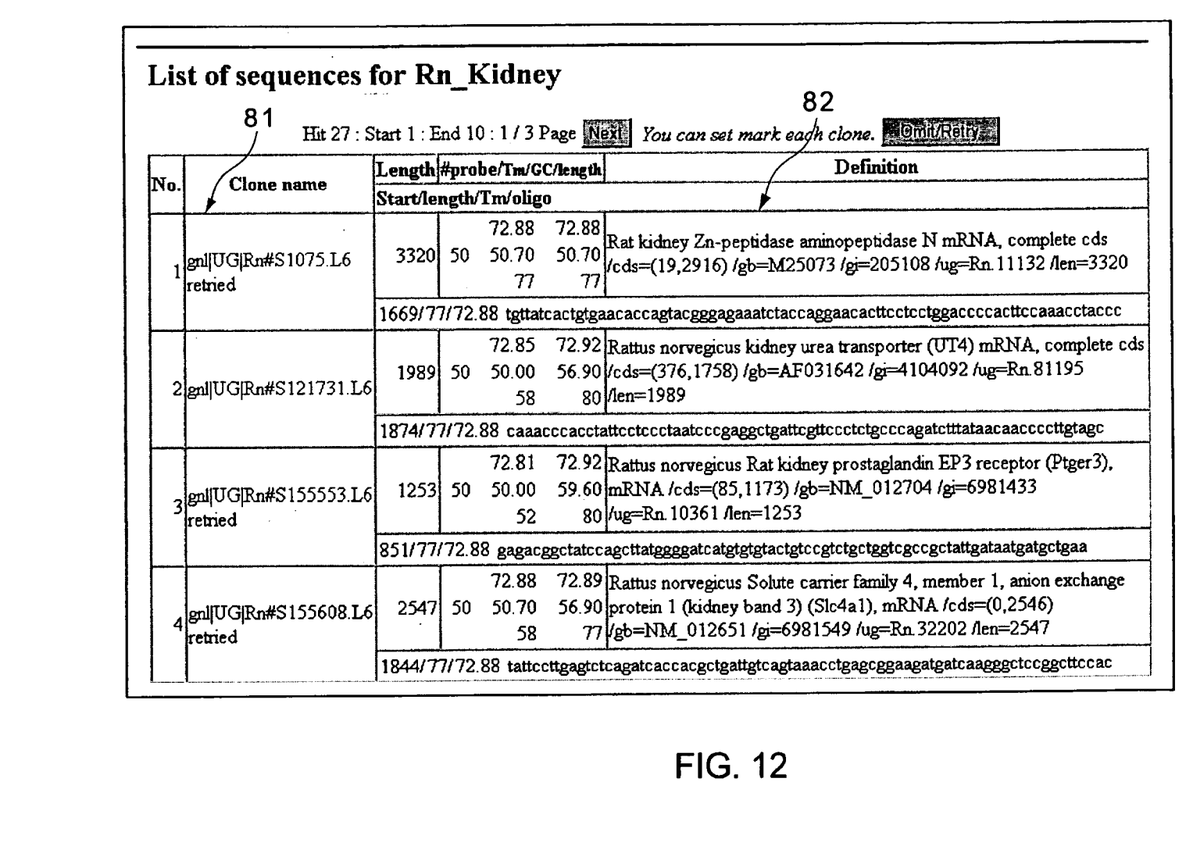
FIG. 12 illustrates a screen display of re-designing results.

Then, when the user tries to go back to the designing result display in FIG. 8, the aforementioned voiding process unit 92 will issue to the aforementioned Tm condition filter unit 22 an operation processing command for the applicable base sequence being analyzed. In this manner, this filter unit 22 will redesign an oligonucleic acid sequence without using the similarity discrimination result voided above. In this manner, as illustrated in FIG. 12, an operation will be processed to obtain and display an optimum oligo-nucleic acid sequence for the concerned base nucleic acid sequence being analyzed in the third row. Incidentally, this optimum oligo-nucleic acid sequence will be indicated with a blue band on the aforementioned multiple alignment screen as indicated with Key 112 in FIG. 11.

Incidentally, this method is not the only one that can be adopted to display designing results. If necessary, for instance, they may be sorted (classified) by the length of oligo-nucleic acid base sequence. Or, evaluating the ease of taking a secondary structure, displaying those that are hard to take a secondary structure may be preferably displayed first.

Further, in this embodiment, when the designing has been completed, the processing end/error notifying unit 25 illustrated in FIG. 1 will produce an E-mail notifying that the process has ended and send the E-mail to the user. In this manner, the user will not have to wait in front of the computer until the process has been completed. Designing of oligo-nucleic acid base sequences in general requires a considerable length of time. The user will be able to process other tasks during the time without worrying about the designing process. Further, in the configuration of this embodiment, a similar notification will be made also when errors occur in the processing due to some cause and the processing has been terminated in the middle.

Figure 6:
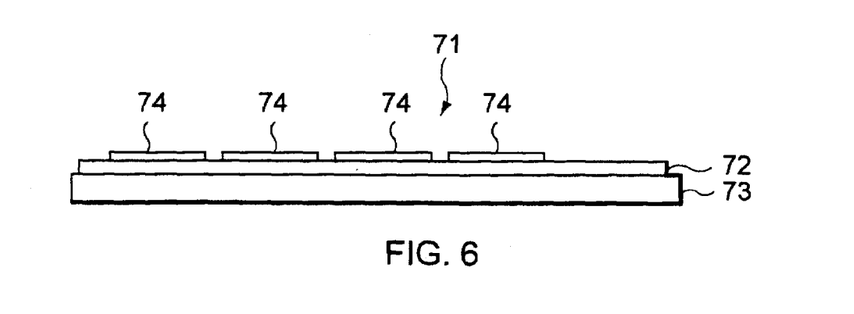
FIG. 6 is a front view illustrating an oligo-nucleic acid array obtained by this embodiment.

FIG. 6 illustrates an oligo-nucleic acid array 71 on which the oligo-nucleic acid base sequences determined in this embodiment are mounted. This oligo-nucleic acid array 71 is comprised by respectively mounting in predetermined compartments 74 the sequences selected from the aforementioned oligo-nucleic acid base sequence candidates using a spot device on a glass substrate 73 comprised by coating poly L lysine 72. According to this type of oligo-nucleic acid array 71, although the lengths of oligo-nucleic acid base sequences are different from one compartment 74 to another, because each spot is within the appropriate Tm range, very easy-to-use and stable results with no miss-hybridization can be obtained.

In this embodiment, an example was illustrated wherein oligo-nucleic acid base sequences are mounted on a glass substrate 73. However, for the substrate, other material such as a resin may be used instead of glass. Also, similar effects can be realized in an array wherein the sequence is spotted to membrane or any two-dimensional array wherein each oligo-nucleic acid base sequence is embedded in a partitioned region so as to be present in an individual area.

Obviously, many modifications and variations of the present invention are possible in light of the above teachings. It is therefore to be understood that, within the scope of the appended claims, the invention may be practiced otherwise than as specifically described.

Figure 7:
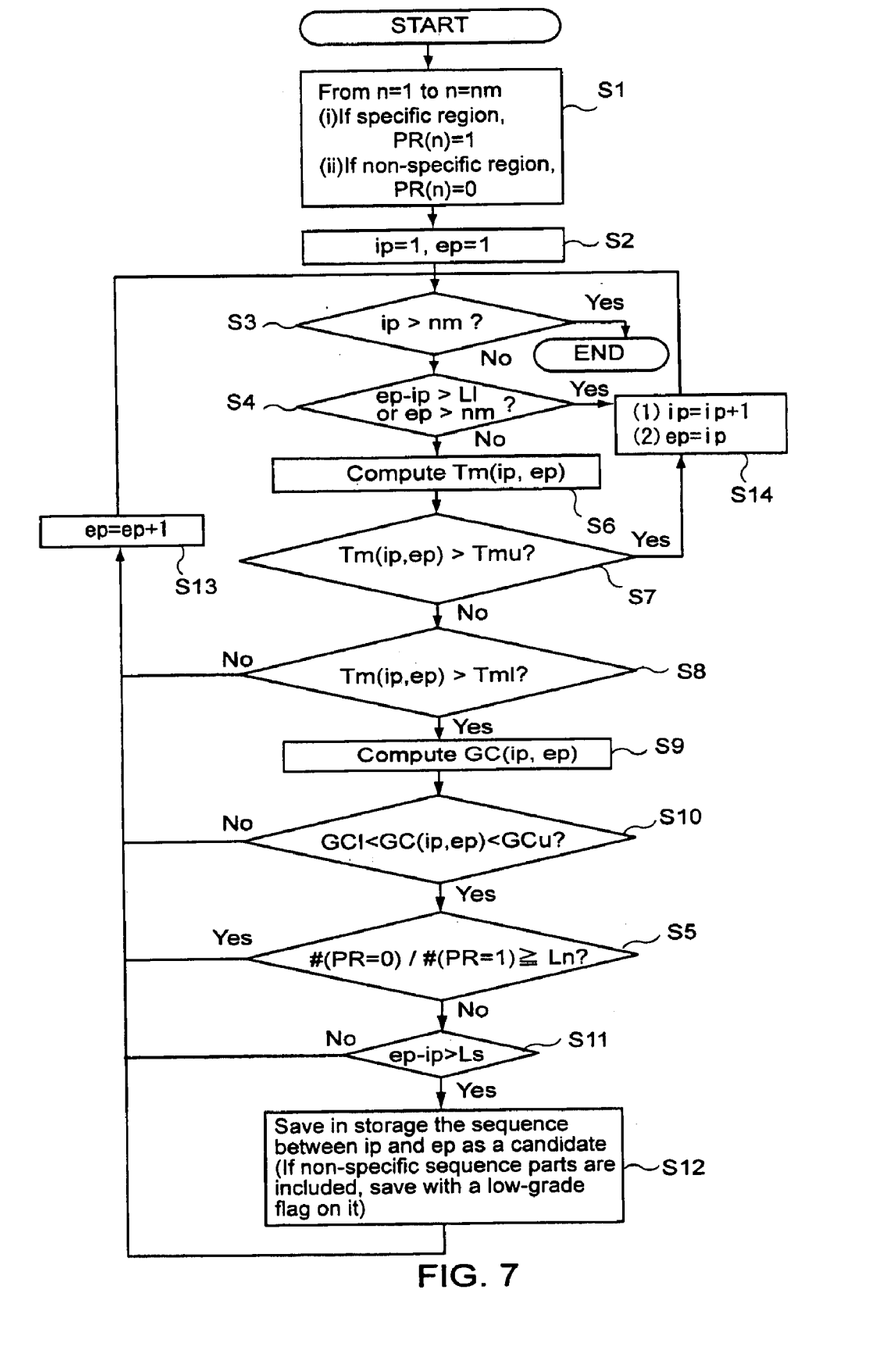
FIG. 7 is a flow chart to explain the procedure for determining an oligo-nucleic acid sequence pertaining to another embodiment.

For instance, in an embodiment above, before the Tm was obtained, the nonspecific region was skipped by executing Step S5. However, the scope of the invention is not limited to this method. That is, in this method, the head of an oligo-nucleic acid base sequence candidate will always be a specific sequence part; however, it may start from a non-specific part. Thus, for instance, as illustrated in FIG. 7, the aforementioned step S5 may be executed after Step S9 of the aforementioned embodiment. the aforementioned embodiment.

According to this configuration, irrespective of whether the first base is a specific sequence part or a non-specific sequence part, as long as the ratio of non-specific part to specific part is Ln (for instance 50%) or smaller, the sequence will be saved as a candidate. Incidentally, candidates partially containing non-specific sequence parts like this example will be outputted as low-grade candidates (Step S10). In this manner, it will be possible to increase the number of candidates that meet the condition as much as possible.

Further, in the embodiment above, the aforementioned system automatically determines that the nucleic acid base sequences being compared having a high percentage of duplication with the nucleic acid base sequence being analyzed based on the similarity discrimination results as duplicate registration, and automatically voids them. However, this is not the only method. The system does not have to automatically void the sequences; it may be configured so that all such sequences will be manually voided through the multiple alignment display. It may also be configured so that the aforementioned percentage of duplication can be varied in any direction based on the similarity discrimination results so as to move the range of nucleic acid base sequences to be voided, thereby to succeed in the designing of an oligo-nucleic acid base sequence.

As explained above, according to the present invention, a system and a method to concurrently determine many oligo-nucleic acid sequences having a high level of accuracy can be obtained.

What is claimed is:

1. A computer software program to design oligo-nucleic acid sequence candidates which bind a reference nucleic acid sequence being analyzed, said reference nucleic acid sequences being stored in memory, said program comprising:
   a) a first command for setting upper and lower limits of
      i) Tm,
      ii) base sequence length and
      iii) GC content;
   in memory; and
   b) a second command for performing homology comparison between said reference nucleic acid sequence being analyzed and a plurality of related nucleic acid sequences and for storing in memory a result from said homology comparison, said result including a specific sequence part that is specific to the nucleic sequence being analyzed; and
   c) a third command for performing, based on said homology comparison, a nucleotide base extension of a partial sequence from said reference nucleic acid sequence being analyzed, so that said partial sequence includes said specific sequence part, and wherein said third command determines whether or not said extended partial sequence is of a length which falls within the limits set in the first command, and outputting those partial sequences which satisfy the limits of i, ii, and iii as oligo-nucleic acid base sequence candidates.

2. The program according to claim 1, said program further comprising a fourth command which notifies a user that the outputting of oligo-nucleic acid sequence candidates for said nucleic acid base sequences being analyzed has been completed.

3. The program of claim 1, wherein said first command further comprises storing a priority order of i, ii, and iii and wherein the program comprises a third command for displaying oligo-nucleic acid sequence candidates outputted in b) in said priority order, along with the Tm, sequence length and GC content values thereof.

4. A computer software program for performing a homology comparison between a registered plurality of nucleic acid base sequences, thereby to design an oligo-nucleic acid sequence candidate which binds a specific nucleic acid sequence being analyzed within a defined Tm range; said computer software program comprising
   a) a first command to store the comparison results between said nucleic acid base sequences in memory; and
   b) a second command for renewing the comparison results by selectively voiding non-specific comparison results from said stored comparison results.

5. The program according to claim 4, said program further comprising
   c) a third command for designing an oligo-nucleic acid sequence candidate which binds said specific nucleic acid base sequence being analyzed after renewal of said stored comparison results.

6. The program according to claim 4, wherein the second command further comprises
   a command for retrieving the comparison results from memory and displaying, in a predetermined format, the homologous part of each sequence compared with the nucleic acid sequence being analyzed; and
   an additional command to selectively void comparison results including this homologous nucleic acid sequence.

7. The program according to claim 4, further comprising a fourth command for detecting nucleic acid base sequences identical to the nucleic acid base sequence being analyzed which are registered in duplication in the plurality of nucleic acid base sequences; and wherein the second command renews the comparison results by voiding the duplicate nucleic acid base sequences in memory.

8. The program according to claim 4, said program further comprising
   a fifth command for inputting upper and lower limits of
     i) Tm,
     ii) base sequence length and
     iii) GC content,; and
   a sixth command for designing oligo-nucleic acid sequence candidates which satisfy the limits specified and which bind the nucleic acid base sequence being analyzed.

9. The program of claim 8, wherein said fifth command further comprises assigning a priority order of i, ii, and iii in memory and wherein said program further comprises a seventh command for displaying in said priority order, the plurality of oligo-nucleic acid sequence candidates designed.

10. A processing method to design, oligo-nucleic acid sequence candidates which bind a nucleic acid reference sequence said method comprising:
   a) a first step for setting upper and lower limits of
     i) Tm,
     ii) base sequence length and
     iii) GC content, in memory; and
   b) a second step for performing homology comparison between said reference nucleic acid sequence being analyzed and a plurality of related nucleic acid sequences and for storing in memory a result from said homology comparison, said result including a specific sequence part that is specific to the nucleic sequence being analyzed; and
   c) a third step for performing, based on said homology comparison, a nucleic acid base extension of a partial nucleic acid sequence from said reference sequence so that said partial sequence includes said specific sequence is part, and
   wherein said third step determines whether or not said extended partial sequence of a length within the limits set in the first step, and outputting those partial sequences as oligonucleic acid sequence candidates.

11. The method according to claim 10, said method further comprising a fourth step which notifies a user that the outputting of oligo-nucleic acid sequence candidates for said nucleic acid base sequences being analyzed has been completed.

12. The method of claim 10, wherein said first step further comprises storing a priority order of i, ii, and iii and wherein the method comprises a third step for displaying oligo-nucleic acid sequence candidates outputted in b) in said pr sequence length and GC content values thereof.

13. A processing method to execute, using a computer, homology comparison between a registered plurality of nucleic acid base sequences, thereby to design oligo-nucleic acid sequence candidates which bind a specified nucleic acid base sequence within a defined Tm range; said method comprising
   a) a first step to store the comparison results in memory for all nucleic acid sequences being analyzed; and
   b) a second step for renewing the comparison results by selectively voiding nonspecific comparison results from said stored comparison results.

14. The method according to claim 13, said method further comprising
   c) a third step for designing oligo-nucleic acid sequence candidates which bind a specified nucleic acid base sequence being analyzed after renewal of said comparison results.

15. The method according to claim 13, wherein the second step further comprises a step for retrieving the comparison results from the memory and displaying, in a predetermined format on the screen the homologous sequence regions of each sequence compared with the reference sequences being analyzed; and a step to selectively void comparison results having said homologous sequence regions.

16. The method according to claim 13, said method further comprising a fourth step to detect, nucleic acid sequences identical to the nucleic acid sequence being analyzed which are registered in duplication in the plurality of nucleic acid base sequences being compared; and wherein the second step renews the comparison results by voiding the duplicate nucleic acid base sequences in memory.

17. The method according to claim 13, said method further comprising
   a fifth step for inputting upper and lower limits of
     i) Tm,
     ii) base sequence length and
     iii) GC content in memory; and
   a sixth step for designing oligo-nucleic acid sequence candidates which satisfy the limits specified and which bind the nucleic acid sequences being analyzed.

18. The method of claim 17, wherein said fifth step further comprises assigning a priority order of i, ii, and iii in memory and wherein said program further comprises a seventh step for displaying in said priority order, the plurality of oligo-nucleic acid sequence candidates designed.

* * * * *

SEQUENCE LISTING

<160> NUMBER OF SEQ ID NOS: 4

<210> SEQ ID NO 1
<211> LENGTH: 77
<212> TYPE: DNA

-continued

```
<213> ORGANISM: Rattus

<400> SEQUENCE: 1
tgttatcact gtgaacacca gtacgggaga aatctaccag gaacacttcc tcctggaccc     60
cacttccaaa cctaccc                                                    77

<210> SEQ ID NO 2
<211> LENGTH: 77
<212> TYPE: DNA
<213> ORGANISM: Rattus

<400> SEQUENCE: 2
caaacccacc tattcctccc taatcccgag gctgattcgt tccctctgcc cagatcttta    60
taacaacccc ttgtagc                                                   77

<210> SEQ ID NO 3
<211> LENGTH: 77
<212> TYPE: DNA
<213> ORGANISM: Rattus

<400> SEQUENCE: 3
tattccttga gtctcagatc accacgctga ttgtcagtaa acctgagcgg aagatgatca    60
agggctccgg cttccac                                                   77

<210> SEQ ID NO 4
<211> LENGTH: 77
<212> TYPE: DNA
<213> ORGANISM: Rattus

<400> SEQUENCE: 4
gagacggcta tccagcttat ggggatcatg tgtgtactgt ccgtctgctg gtcgccgcta    60
ttgataatga tgctgaa                                                   77
```